(12) United States Patent
Goode et al.

(10) Patent No.: US 9,149,290 B2
(45) Date of Patent: Oct. 6, 2015

(54) VESSEL ENTRY DEVICE

(75) Inventors: Louis B. Goode, Cranberry Township, PA (US); Chun Kee Lui, Monroeville, PA (US); Robert Booker, Vandergrift, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 161 days.

(21) Appl. No.: 11/867,984

(22) Filed: Oct. 5, 2007

(65) Prior Publication Data
US 2008/0071342 A1 Mar. 20, 2008

Related U.S. Application Data

(63) Continuation-in-part of application No. 11/404,666, filed on Apr. 14, 2006.

(60) Provisional application No. 60/671,858, filed on Apr. 15, 2005.

(51) Int. Cl.
*A61B 19/00* (2006.01)
*A61B 17/32* (2006.01)
(Continued)

(52) U.S. Cl.
CPC ..... *A61B 17/32002* (2013.01); *A61B 17/32053* (2013.01); *A61B 17/3468* (2013.01); *A61N 1/056* (2013.01); *A61B 2017/00548* (2013.01); *A61N 2001/0578* (2013.01)

(58) Field of Classification Search
CPC .............. A61B 17/3468; A61B 17/32002; A61B 17/32053; A61B 2017/320024–2017/320032; A61N 1/056; A61N 2001/0578

USPC .......... 606/108, 129, 180, 159, 170, 171; 604/158, 161, 164.01, 164.06, 164.1, 604/164.11, 164.13
See application file for complete search history.

(56) References Cited

U.S. PATENT DOCUMENTS 2,261,230 A 11/1941 Cox et al. ............... 128/310
3,132,549 A 5/1964 Lee ........................ 81/57
(Continued)

FOREIGN PATENT DOCUMENTS

EP 0 807 412 A1 11/1997 ............ A61B 17/32
EP 1820458 A1 8/2007 ............ A61B 17/22
(Continued)

OTHER PUBLICATIONS

Albee, F., "Bone Surgery with Machine Tools," Scientific American, Apr. 1936, pp. 178-181.

*Primary Examiner* — Katherine Rodjom
*Assistant Examiner* — Jonathan Hollm
(74) *Attorney, Agent, or Firm* — Brinks Gilson & Lione

(57) ABSTRACT

An entry device for providing access to the interior of a body vessel through a wall of the vessel to enable removal of an implanted structure, such as a cardiac lead, from the body vessel includes an elongated sheath member and a tip positioned at the distal end of the sheath member. The elongated sheath member and tip have respective passageways extending therethrough that are sized and aligned to receive the implanted structure therein upon accessing the vessel. The elongated sheath member is capable of delivering sufficient torque to permit advancement of the tip through a wall of the vessel. The device may include an optional handle, and may be driven by manual or mechanical action.

24 Claims, 7 Drawing Sheets

(51) Int. Cl.
*A61B 17/3205* (2006.01)
*A61B 17/34* (2006.01)
*A61N 1/05* (2006.01)
*A61B 17/00* (2006.01)

(56) References Cited

U.S. PATENT DOCUMENTS

| | | | | |
|---|---|---|---|---|
| 3,519,046 | A | | 7/1970 | Pierce ............................ 145/66 |
| 3,756,090 | A | | 9/1973 | Mella et al. |
| 4,030,503 | A | * | 6/1977 | Clark, III .................... 606/159 |
| 4,084,594 | A | | 4/1978 | Mosior ........................ 128/311 |
| 4,174,858 | A | | 11/1979 | Brooks ............................ 285/7 |
| 4,576,162 | A | | 3/1986 | McCorkle |
| 4,643,190 | A | | 2/1987 | Heimberger |
| 4,732,154 | A | * | 3/1988 | Shiber .......................... 606/159 |
| 4,943,289 | A | | 7/1990 | Goode et al. |
| 4,988,347 | A | | 1/1991 | Goode et al. |
| 5,011,482 | A | | 4/1991 | Goode et al. |
| 5,013,310 | A | | 5/1991 | Goode et al. |
| 5,052,402 | A | | 10/1991 | Bencini et al. ................ 128/751 |
| 5,092,848 | A | | 3/1992 | deCiutiis ...................... 604/170 |
| 5,122,134 | A | * | 6/1992 | Borzone et al. ................ 606/80 |
| 5,207,683 | A | | 5/1993 | Goode et al. |
| 5,363,726 | A | | 11/1994 | Smith .......................... 81/57.29 |
| 5,423,806 | A | | 6/1995 | Dale et al. |
| 5,447,534 | A | | 9/1995 | Jammet ........................ 607/127 |
| 5,507,751 | A | | 4/1996 | Goode et al. |
| 5,591,187 | A | | 1/1997 | Dekel |
| 5,632,749 | A | | 5/1997 | Goode et al. |
| 5,639,276 | A | * | 6/1997 | Weinstock et al. ............ 606/129 |
| 5,651,781 | A | * | 7/1997 | Grace ................................ 606/1 |
| 5,697,936 | A | | 12/1997 | Shipko et al. |
| 5,769,858 | A | | 6/1998 | Pearson et al. |
| 5,814,044 | A | | 9/1998 | Hooven |
| 5,830,221 | A | | 11/1998 | Stein et al. .................... 606/151 |
| 5,830,231 | A | | 11/1998 | Geiges, Jr. .................... 606/205 |
| 5,913,857 | A | | 6/1999 | Ritchart et al. |
| 5,913,867 | A | * | 6/1999 | Dion ............................ 606/180 |
| 5,980,515 | A | | 11/1999 | Tu |
| 5,980,545 | A | * | 11/1999 | Pacala et al. .................. 606/170 |
| 5,984,939 | A | | 11/1999 | Yoon |
| 5,993,467 | A | | 11/1999 | Yoon |
| 6,010,476 | A | * | 1/2000 | Saadat ............................ 604/22 |
| 6,099,537 | A | | 8/2000 | Sugai et al. |
| 6,135,947 | A | | 10/2000 | Watanabe et al. ............. 600/178 |
| 6,136,005 | A | | 10/2000 | Goode et al. |
| 6,190,353 | B1 | | 2/2001 | Makower et al. |
| 6,283,511 | B1 | | 9/2001 | Kamp .......................... 285/391 |
| 6,332,886 | B1 | | 12/2001 | Green et al. .................... 606/80 |
| 6,419,974 | B1 | | 7/2002 | Silva et al. |
| 6,503,261 | B1 | | 1/2003 | Bruneau et al. ............... 606/159 |
| 6,656,195 | B2 | | 12/2003 | Peters et al. .................. 606/159 |
| 6,687,548 | B2 | | 2/2004 | Goode |
| 6,712,826 | B2 | | 3/2004 | Lui |
| 6,712,855 | B2 | | 3/2004 | Martin et al. ............. 623/20.34 |
| 6,783,533 | B2 | | 8/2004 | Green et al. .................... 606/80 |
| 2002/0143358 | A1 | | 10/2002 | Domingo et al. ............. 606/190 |
| 2002/0172923 | A1 | | 11/2002 | Strong et al. .................. 433/165 |
| 2003/0040787 | A1 | | 2/2003 | Flynn et al. ................... 607/122 |
| 2004/0143287 | A1 | | 7/2004 | Konstantino et al. ......... 606/194 |
| 2004/0260336 | A1 | | 12/2004 | Braun |
| 2005/0107816 | A1 | | 5/2005 | Pingleton et al. ............. 606/185 |
| 2005/0149096 | A1 | | 7/2005 | Hilal et al. .................... 606/191 |
| 2005/0273125 | A1 | | 12/2005 | Opie |
| 2006/0235431 | A1 | | 10/2006 | Goode et al. |
| 2006/0253179 | A1 | | 11/2006 | Goode et al. |

FOREIGN PATENT DOCUMENTS

FR 2 625 429 7/1989
WO WO 02/36022 A1 5/2002

* cited by examiner

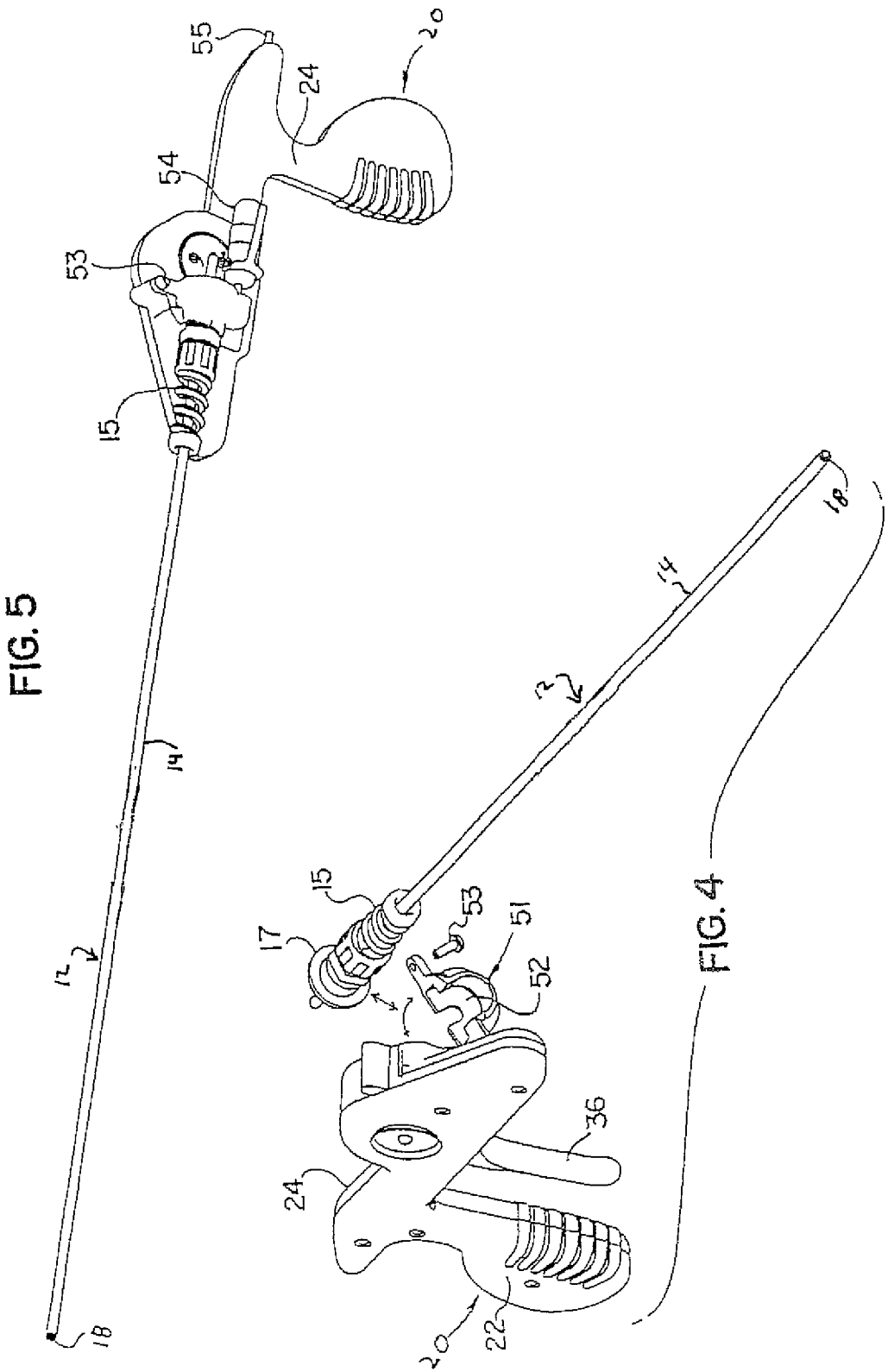

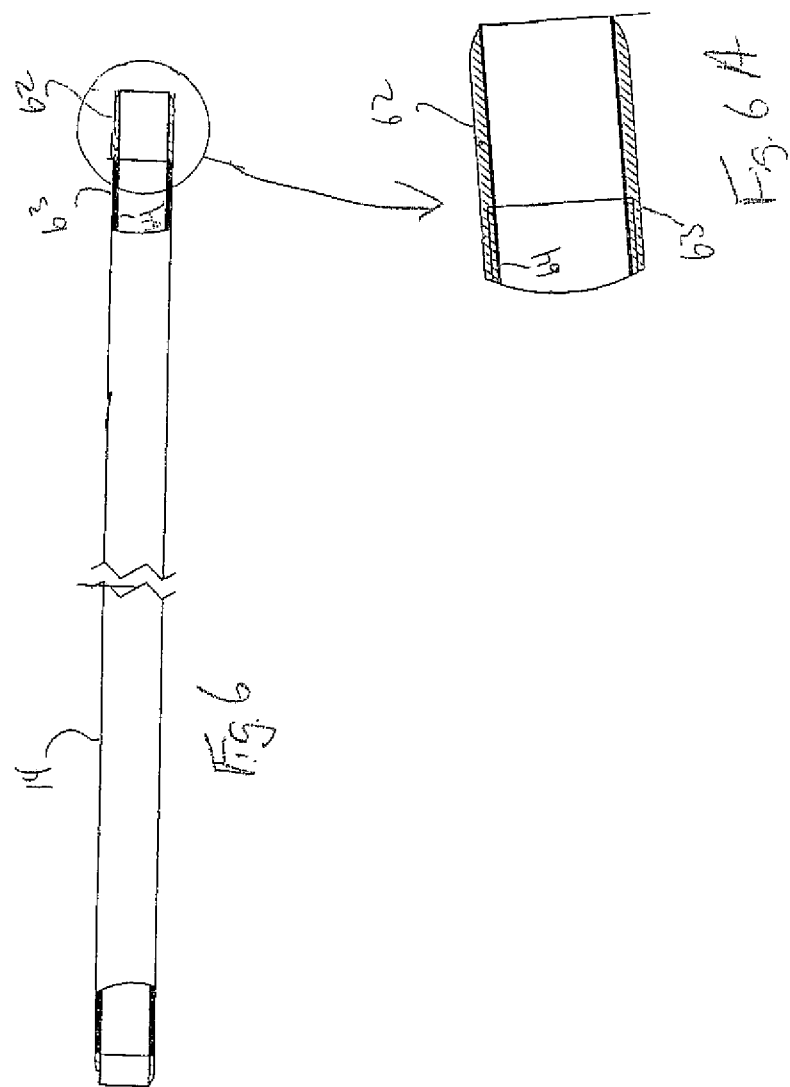

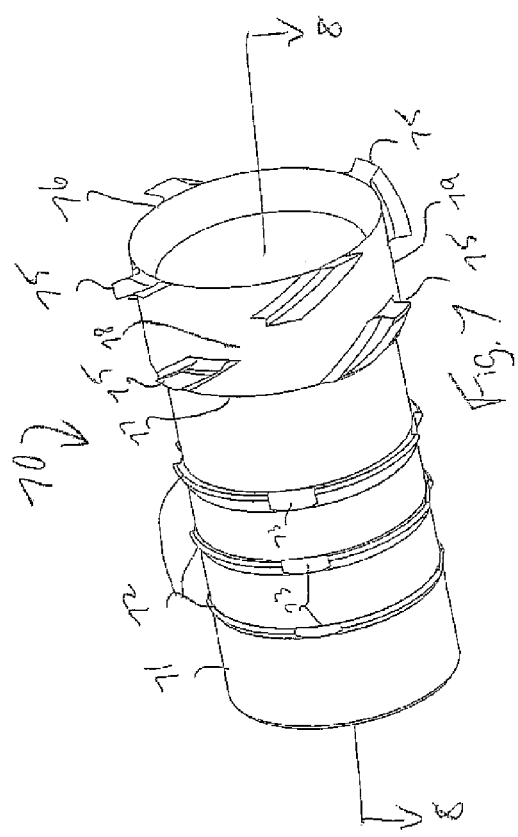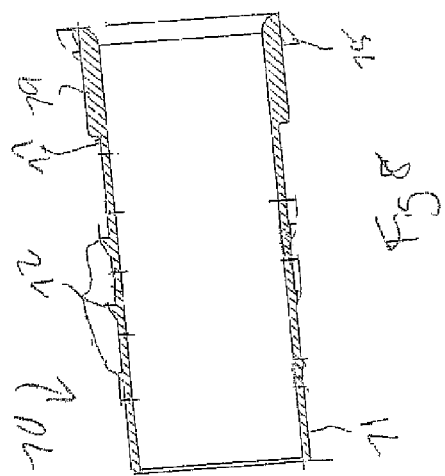

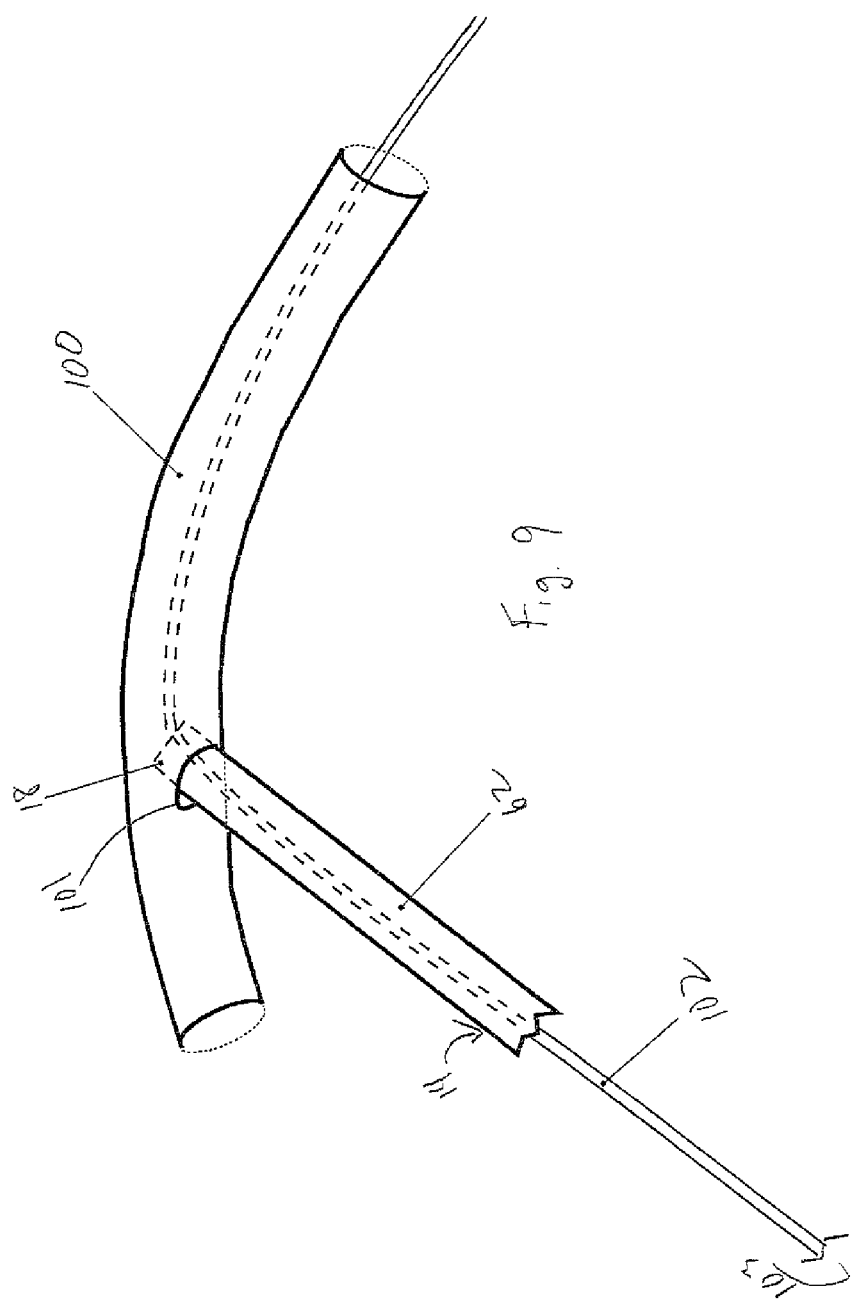

VESSEL ENTRY DEVICE

RELATED APPLICATION

The present patent document is a continuation-in-part application of U.S. patent application Ser. No. 11/404,666, filed Apr. 14, 2006, which claims the benefit of the filing date under 35 U.S.C. §119(e) of Provisional U.S. Patent Application Ser. No. 60/671,858, filed Apr. 15, 2005. Each of the foregoing applications is hereby incorporated by reference.

BACKGROUND

1. Technical Field

This invention relates generally to devices for use in the medical arts. More particularly, the invention relates to a device for use in gaining entry to a body vessel for purposes of removing an elongated indwelling structure, such as an implanted electrical pacemaker or defibrillator lead, from the vessel.

2. Background Information

A variety of medical treatments and surgical methods entail implanting an elongated structure in the body of a human or veterinary patient. Examples of such elongated structures include catheters, sheaths and cardiac electrical leads (such as pacemaker leads and defibrillator leads), as well as a variety of other devices. Over time, it can become necessary or desirable to remove the implanted elongated structure from the body of the patient. However, if the elongated structure has been implanted for an extended period of time, encapsulating biological tissue can grow around the elongated structure, making it difficult to remove the structure from the encapsulating tissue.

A heart pacemaker is typically implanted in a subcutaneous tissue pocket in the chest wall of a patient. A pacemaker lead extends from the pacemaker through a vein into a chamber of the patients heart. The pacemaker lead commonly includes a conductor, such as an electrical wire coil, for conducting electrical signals (such as stimulating and/or sensing signals) between the pacemaker and the heart. Leads for defibrillators are generally similar to pacemaker leads, and are positioned about the heart. Defibrillator leads may be affixed either internally or externally of the heart.

While cardiac electrical leads typically have a useful life of many years, over time such leads may become encapsulated by fibrotic tissue against the heart itself or the wall of the vein, or against other surrounding tissue. Encapsulation is especially encountered in areas where the velocity of the flow of blood is low. The fibrotic tissue can be very tough, which makes it difficult to remove the lead from the area of the heart without causing trauma to the area. When small diameter veins through which a pacemaker lead passes become occluded with fibrotic tissue, separation of the lead from the vein can cause severe damage to the vein, including the possible dissection or perforation of the vein. In such cases, separation of the lead from the vein is usually not possible without restricting or containing movement of the lead, i.e., fixing the lead in position with respect to the patient, in particular, with respect to the patients vein.

To avoid this and other possible complications, some useless cardiac leads are simply left in the patient when the pacemaker or defibrillator is removed or replaced. However, such a practice can incur the risk of an undetected lead thrombosis, which can result in stroke, heart attack, or pulmonary embolism. Such a practice can also impair heart function, as plural leads can restrict the heart valves through which they pass.

There are many other reasons why removal of a useless lead may be desirable. For example, if there are too many leads positioned in a vein, the vein can be obstructed to the extent that fluid flow through the vein is severely compromised. In addition, multiple leads can be incompatible with one another, thereby interfering with the pacing or defibrillating function. An inoperative lead can migrate during introduction of an adjacent second lead, and mechanically induce ventricular arrhythmia. Other potentially life-threatening complications can require the removal of the lead as well. For example, removal of an infected pacemaker lead may be desirable so as to avoid conditions such as septicemia or endocarditis.

Surgical removal of a heart lead in such circumstances may require open heart surgery. However, open heart surgery is accompanied by significant risk and cost to the patient, as well as a potential for unintended complications. A variety of methods and apparatuses have been devised as alternatives to open heart surgery for heart lead removal. Several of these methods and apparatuses are described in related patents, such as U.S. Pat. No. 5,697,936, titled "Device for Removing an Elongated Structure Implanted in Biological Tissue"; U.S. Pat. No. 5,507,751, titled "Locally Flexible Dilator Sheath"; U.S. Pat. No. 5,632,749, titled "Apparatus for Removing an Elongated Structure Implanted in Biological Tissue"; U.S. Pat. No. 5,207,683, titled "Apparatus for Removing an Elongated Structure Implanted in Biological Tissue"; U.S. Pat. No. 4,943,289, titled "Apparatus for Removing an Elongated Structure Implanted in Biological Tissue"; U.S. Pat. No. 5,011,482, titled "Apparatus for Removing an Elongated Structure Implanted in Biological Tissue"; U.S. Pat. No. 5,013,310, titled "Method and Apparatus for Removing an Implanted Pacemaker Lead"; U.S. Pat. No. 4,988,347, titled "Method and Apparatus for Separating a Coiled Structure from Biological Tissue"; U.S. Pat. No. 5,423,806, titled "Laser Extractor for an Implanted Object"; U.S. Pat. No. 6,419,674, titled "Radio Frequency Dilator Sheath", and U.S. Pat. Nos. 6,687,548 and 6,712,826, each titled "Apparatus for Removing an Elongated Structure Implanted in Biological Tissue", among others. Each of the aforementioned patents is incorporated by reference as if fully set forth herein.

Most of the aforementioned patents describe manual, or mechanical, devices that are used for removing an implanted structure, such as a pacemaker lead. Others describe newer non-mechanical techniques, such as laser extraction and radio frequency extraction. These newer techniques have been effective in many cases when the amount and/or placement of fibrous growth that surrounds the implanted lead render manual extraction difficult or impossible. One example of an effective device that uses radio frequency extraction to enable the physician to cut away the heavy growth is the PERFECTA® electrosurgical dissection sheath, available from Cook Vascular Incorporated, of Leechburg, Pa. The PERFECTA® sheath utilizes an intermittent discrete RF dissecting arc between bipolar electrodes located at the sheath's distal end. This sheath enables the physician to separate, with directed precision, a transvenous lead from its fibrous binding attachments.

Although the prior art devices have been found to be effective in many situations, physicians continue to encounter particularly difficult situations in which existing extraction devices provide unsatisfactory or inconsistent results. Due to the multiplicity of factors that may contribute to the difficulty in extracting an implanted lead, a technique that may be effective in one instance, may not provide similarly successful results in another instance. For example, manual devices normally are provided with single or telescoping flexible sheaths. Such sheaths, generally formed from a polymer, have the flexibility to enable the sheath to traverse tortuous pathways in the vessel. However, such sheaths may lack sufficient strength to cut through particularly tough tissue growth and calcification around the implanted lead. Laser and radio frequency devices normally utilize metallic sheaths. Such sheaths provide a good deal of strength to enable the sheath to cut through fibrous growths. However, some growths are resistant to metallic sheaths, and these sheaths may also lack the flexibility desired to maneuver tortuous pathways.

In order to address these and other difficulties, incorporated-by-reference U.S. patent application Ser. No. 11/404,666 discloses novel extraction devices and tip structures that have been found to be very effective in removing implanted leads from a vessel. Such devices are well able to traverse tortuous curves in the vessel, and are provided with a non-aggressive tip that primarily disrupts, rather than cores or cuts, the obstruction away from the vessel. By gently disrupting the obstruction, rather than cutting or coring it, the tips have a reduced propensity to cut a lead or breach a vessel wall.

Although the devices and tips described hereinabove have generally been found to be effective is removing implanted leads and other indwelling structures from a vessel, difficulties may be encountered in initially gaining access to the vessel, such as a vein, in order to facilitate insertion of the removal device. Lead removal tools such as the electrosurgical dissection and laser sheaths described above, as well as the sheaths and tips described in the incorporated-by-reference documents, are often not particularly efficacious in gaining access to the vessel. Such devices are normally designed to be flexible so that they can negotiate the potentially tortuous curves of the vessel. In order to position the tip of these flexible devices over the desired entry point into the vessel, the physician often needs to grasp the device close to the distal tip by hand, which may block the physician's vision of the entry point. Manipulation of the device, such as by pushing or turning, may require the physician to also grasp the proximal end of the device. Therefore, two hands are typically required to operate such devices.

A device specifically designed to gain access to a body vessel, such as a blood vessel, to assist in removal of an indwelling structure is manufactured and sold commercially by Cook Vascular Incorporated. This device comprises a set of telescoping stiff metal tubes. This device has sufficient stiffness to enable the physician to position its distal tip at the vessel wall without having to grasp the distal end of the device. However, its efficacy is derived by forcefully pushing and turning the device, which action can be ergonomically challenging for some individuals.

It is desired to provide a device for use in gaining entry to a body vessel for removing an indwelling structure that avoids the problems of prior art devices.

BRIEF SUMMARY

The problems of the prior art are addressed by the inventive vessel entry device. In one form thereof, the present invention comprises an entry device for providing access to a body vessel for removing an elongated indwelling structure therefrom. The device comprises an elongated sheath and a tip positioned at a distal end of the sheath. The elongated sheath and tip have respective passageways extending therethrough, which passageways are sized and aligned such that the indwelling structure is receivable therein. The elongated sheath has a rigidity sufficient to permit advancement of the tip through a wall of the vessel rotational and axial movement of the sheath proximal end. The tip has a distal end configured for entry through the vessel wall. If desired, the device may include a handle configured for engagement with a proximal end of the sheath. The handle may be provided with an actuator and a drive mechanism responsive to the actuator, wherein the drive mechanism is operable for selectively translating input of the actuator into rotational and/or axial movement of the sheath.

In another form thereof, the present invention comprises a method of providing entry to a body vessel for removing an elongated indwelling structure therefrom, wherein the elongated indwelling structure has a distal end disposed within the body vessel and a proximal end extending through an opening in the vessel, and wherein the opening is sized and configured to inhibit removal of the distal end of the indwelling structure from the vessel. The method includes the steps of providing a vessel entry device comprising an elongated sheath and a tip positioned at a distal end of the sheath, the elongated sheath and tip having respective passageways extending therethrough, the passageways sized and aligned such that the proximal end of the indwelling structure is receivable therein, the elongated sheath having a rigidity sufficient to permit advancement of the tip through a wall of the vessel by at least one of rotational and axial movement of the sheath proximal end; introducing the distal end of the tip over the extending proximal end of the indwelling structure, and advancing the vessel entry device to the vessel wall; and passing the tip and a distal portion of said sheath through the vessel opening.

BRIEF DESCRIPTION OF THE DRAWINGS

FIG. 4 is a view showing the handle and sheath of the vessel entry device prior to assembly;

FIG. 5 is a view of the reverse side of an embodiment of a vessel entry device including a power supply;

FIG. 6 is a side view of a sheath of a vessel entry device according to the present invention;

FIG. 6A is an enlarged view of the distal end portion of the sheath of FIG. 6;

FIG. 7 is a perspective view of one embodiment of a distal tip for use with the vessel entry device of FIG. 1;

FIG. 8 is a longitudinal sectional view of the tip of FIG. 7; and

FIG. 9 is a view of a body vessel with a cardiac lead protruding from an opening in the vessel, and the inventive device fitted over the lead and penetrating the vessel through the opening.

DETAILED DESCRIPTION OF THE DRAWINGS AND THE PRESENTLY PREFERRED EMBODIMENTS

Figure 1:
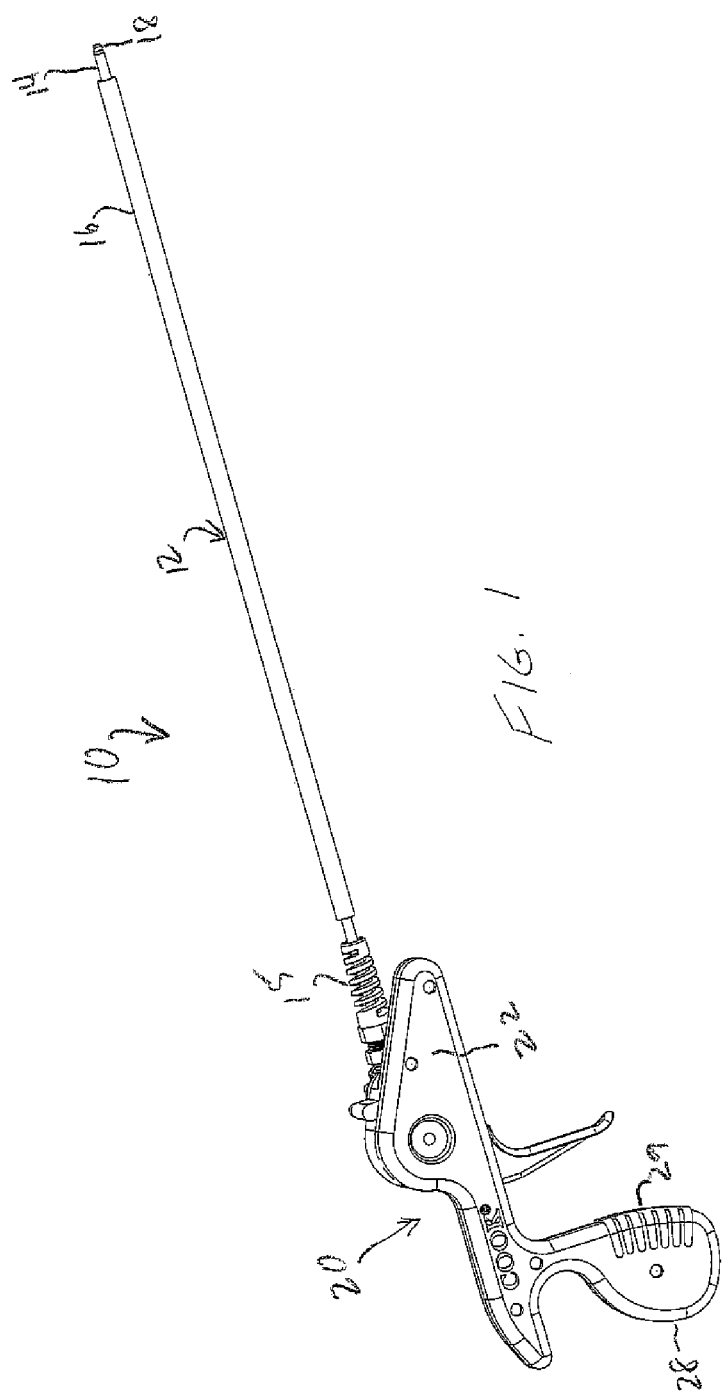
FIG. 1 is a perspective view of one embodiment of a vessel entry device of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention relates to an entry device for use in providing access to a vessel for removing an elongated indwelling structure from the vessel. In the following discussion, the terms "proximal" and "distal" will be used to describe the opposing axial ends of the vessel entry device, as well as the axial ends of various component features of the device. The term "proximal" is used in its conventional sense to refer to the end of the device (or component thereof) that is closest to the operator during use of the device. The term "distal" is used in its conventional sense to refer to the end of the device (or component) that is at the greatest distance from the operator, or that is initially inserted into the patient.

The indwelling elongated structure targeted for removal may comprise a cardiac lead. A cardiac lead, as the term is used herein, refers to a lead that is used in connection with a heart-related device. Non-limiting examples of cardiac leads include pacemaker leads, defibrillator leads, coronary sinus leads, and left ventricular pacing leads. In addition to cardiac leads, other indwelling structures targeted for removal may include neurological pacing and stimulation leads, as well as various other implanted catheters, sheaths, cannulae and the like. For convenience, the following discussion will refer to the use of the vessel entry device in a process for removal of a cardiac lead, such as a pacemaker or a defibrillator lead. However it should be understood that this is no way intended to be a limitation on the scope of the invention.

FIG. 1 is a perspective view of a preferred embodiment of a vessel entry device 10 for providing access to the interior of a body vessel to remove an indwelling structure, such as a cardiac electrical lead, from the vessel. In this embodiment, vessel entry device 10 includes a sheath member 12 comprising inner and outer coaxial sheaths 14, 16, a distal tip 18, and an optional handle 20. Although many users may find the handle to be convenient in providing rotary and/or axial action to the sheath, other users may prefer to manually rotate and/or advance the sheath into the vessel. Therefore, vessel entry device 10 may, or may not, include a handle.

Although FIG. 1 illustrates a sheath 12 having inner and outer sheath members 14, 16, the presence of the outer sheath member is also optional, and the sheath may simply comprise (inner) sheath member 14. When present, outer sheath member 16 is typically free floating in the device, or in other words, is not affixed to other portions of the device. However, the presence of an outer sheath member 16 that covers a majority of the length of the inner sheath member 14 as shown is preferred, as it generally increases the utility of the device. The presence of the outer sheath member can prevent other objects, such as other indwelling devices (pacing leads, etc.), from interfering with the inner sheath member as the inner member rotates, in the manner to be described. The outer sheath member can also aid in dilating the vessel entry site to allow for smoother entry and reentry of subsequent extraction devices. In addition, if the primary lead anchoring location is at the vessel entry site, the lead may readily slide out once the device gains vessel access. In this instance, the outer sheath functions as a conduit in allowing the lead to be drawn past tortuous regions (such as the tight clavicular region), and out of the body.

Figure 2:
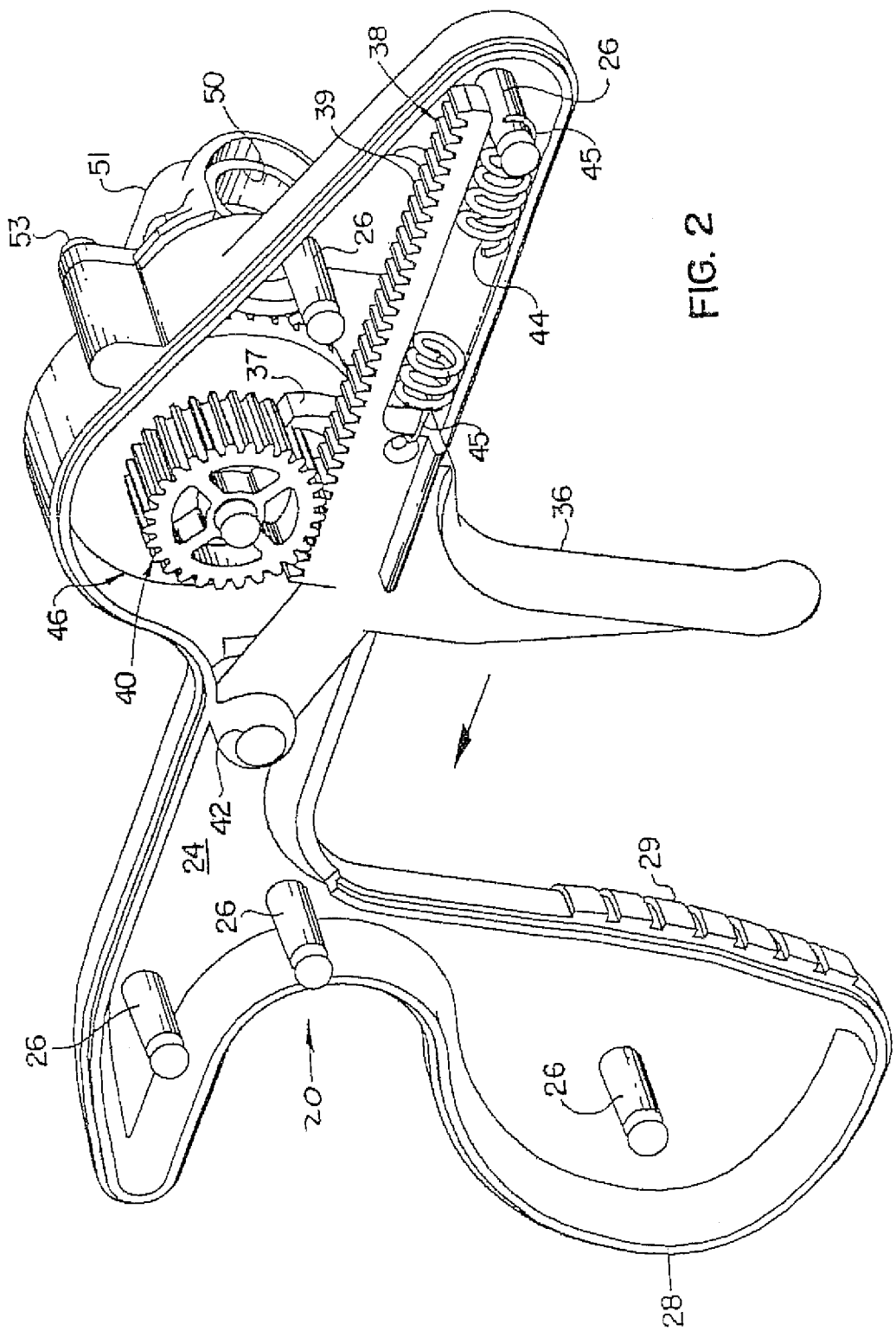
FIG. 2 is a perspective view of the handle of the vessel entry device of FIG. 1, with a portion of the outer wall removed to illustrate the inner components of the handle.

In the embodiment shown, handle 20 includes opposing handle walls 22, 24. FIG. 2 is a perspective view of handle 20 wherein handle outer wall 22 has been removed to provide visualization of the internal workings of this handle. Handle walls 22, 24 are connected via a snap fit or other conventional mechanism. In the embodiment shown, handle wall 24 includes a plurality of transverse pegs 26 that are received in corresponding receptacles (not shown) in handle wall 22. Handle 20 may be provided with an ergonomically shaped grip 28, as shown in the figures. If desired, ergonomic grip 28 may also include a plurality of ribs 29 spaced along a hand-engaging surface of grip 28. An optional strain relief 15 may be provided at the proximal end of sheath member 14 to inhibit kinking of the sheath during use of device 10.

Figure 3:
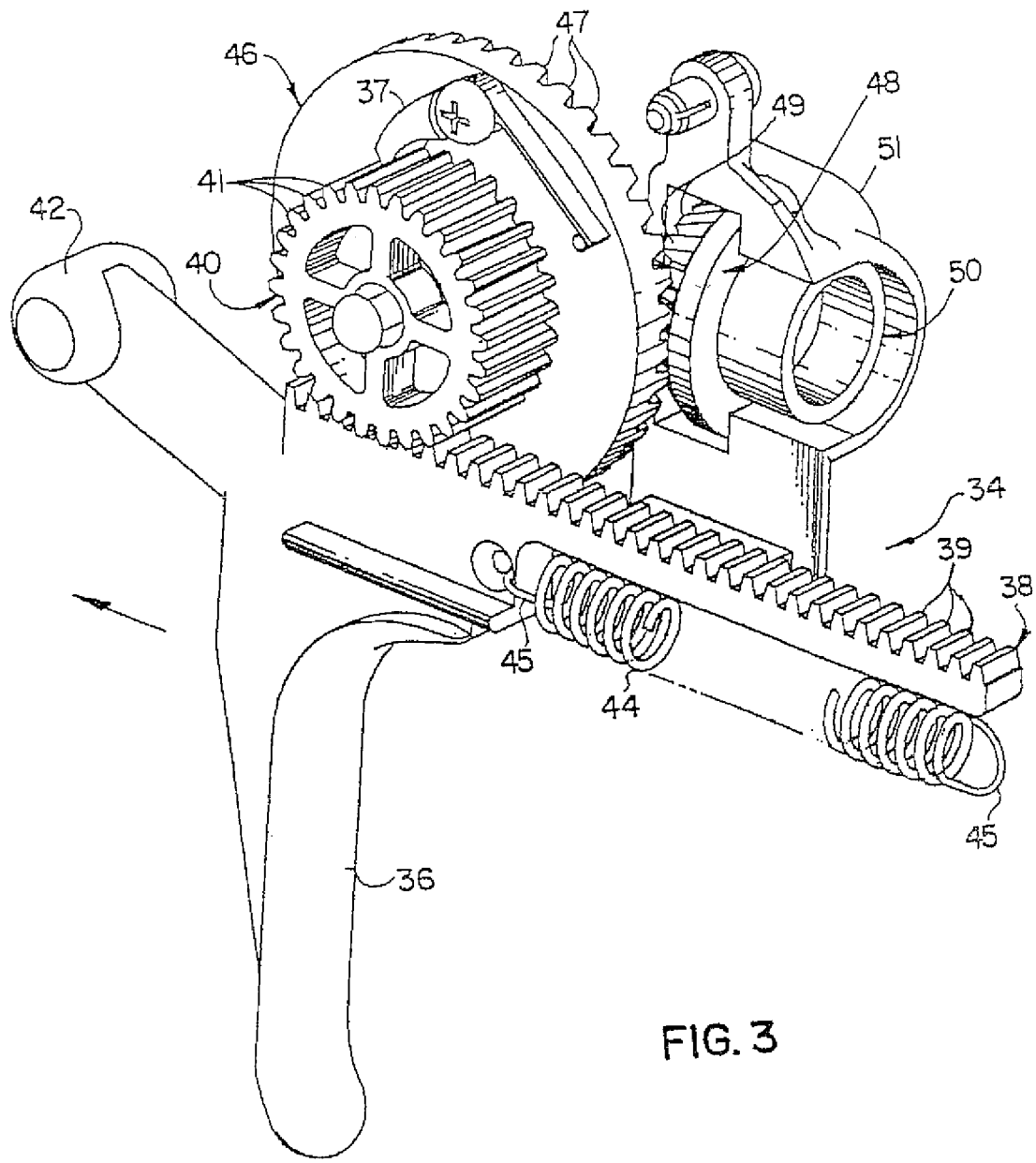
FIG. 3 is a view of the translation device removed from the handle of the vessel entry device.

In the embodiment shown in FIGS. 2 and 3, handle 20 includes a translation mechanism 34. For ease of viewing, in FIG. 3 translation mechanism 34 has been removed from the wall members of the handle. Translation mechanism 34 utilizes a rack and gear structure to translate linear motion generated upon pull of an actuator, such as trigger 36, into rotational motion on the part of sheath member 14. Translation mechanism 34 includes a rack 38 having a plurality of teeth 39 as shown. Rack 38 is engaged with trigger 36, such that upon the operator pulling trigger 36 in the proximal direction (as indicated by the arrow), rack 38 likewise is urged linearly in the proximal direction.

An external spur gear 40, having a plurality of teeth 41, is aligned with rack 38 such that spur gear teeth 41 mesh with rack teeth 39. Linear movement of rack teeth 29 therefore causes spur gear 40, and thus teeth 41, to rotate in the direction shown. A pawl 37 may be provided to inhibit undesired (counter-clockwise) rotation of the gear. Pawl 37 may also be configured to create ratcheting action upon movement of rack 38 and spur gear 40, and to provide an audible confirmation of the rotation of the spur gear. A stabilizing arm 42 extending in a proximal direction from rack 38 may be provided to maintain proper orientation of rack 38 in handle 20, and to ensure smooth movement of the trigger without bending or flexing when pulled under a load. Preferably, a spring 44 is affixed at one end to rack 38 and at the other end to housing wall peg 26 (distal of rack 38), for urging trigger 36 back to the position shown in FIG. 2 upon relaxation of the tension resulting from the trigger pull by the operator. Spring 44 may be retained in handle 20 by any conventional means, such as hooks 45.

Spur gear 40 is affixed to large bevel gear 46, in a manner such that rotation of spur gear 40 causes a corresponding rotation of large bevel gear 46. Large bevel gear 46 includes a plurality of teeth 47 on a side of large bevel gear 46 opposite spur gear 40. Small bevel gear 48 is rotationally aligned with large bevel gear 46 in conventional fashion, such that large bevel gear teeth 47 mesh with small bevel gear teeth 49 as illustrated. Teeth 47 and 49 are aligned in conventional fashion for such bevel gears, in this case at an angle of about 90 degrees. As a result, the direction of rotation is translated via said gears along the 90 degree angle. Hub 50 is affixed to the side of small bevel gear 48 opposite teeth 49 for rotation in accordance with the rotation of small bevel gear 48. Hub 50 is sized and shaped to securely receive a proximal end of inner sheath member 14, by conventional means such as adhesion, friction and/or threading.

Preferably, sheath 12 is engaged with handle 20 in a manner such that it may be selectively affixed to, or removed from, handle 20. FIG. 4 illustrates one preferred manner in which sheath 12 may be removably affixed in handle 20. In this figure, optional outer sheath member 16 has been removed, and sheath 12 simply comprises elongated sheath member 14. Hub 50 is not visible in the orientation of FIG. 4. In this embodiment, wall member 24 includes a pivotable wall portion 51 that may be pivoted to the open position as shown, and sheath member 14 is provided with a flange 17 at the proximal end of sheath member 14, to seat the sheath in the hub. When the sheath is affixed in hub 50, flange 17 is snugly received against a surface 52 of pivotable portion 51. When portion 51 is pivoted into the closed position, a conventional latching mechanism, such as a screw 53 is provided to maintain pivotable portion 51 in the closed position (FIG. 5), thereby retaining sheath 12 in handle 20. Those skilled in the art will appreciate that there are numerous other ways in which the sheath may be held in the handle, and that the particular removable affixation mechanism described herein is not crucial to the invention.

Thus, as has been shown, sheath 12 may be selectively attached to, and detached from, handle 20. With this feature, sheath 12 and tip 18 may be removed from handle 20 following entry of the tip into the vessel and replaced with another sheath and tip, such as any of the sheaths and tips disclosed in the incorporated-by-reference application Ser. No. 11/404,666, for use in separating the elongated indwelling structure from encapsulating tissue; However, the device can likewise be structured such that the sheath and tip are permanently affixed in the device. In this event, the device would typically be discarded following use.

During manual operation of device 10 shown in FIGS. 1-4, the operator pulls trigger 36 in the linear direction shown. As discussed, this action drives, or translates, the linear motion of the trigger pull to rotary movement of hub 50, thereby causing rotation of sheath 12. Rack and gear structures are well known in the art. The remaining features of the translation mechanism not described herein are conventional, and need not be further explained or illustrated to enable one skilled in the art to utilize the mechanism for the purposes described. In addition, those skilled in the art will appreciate that there are numerous other ways in which a manual device can be structured such that an action generated by an operator, such as the trigger pull described herein, may be translated to rotary or axial motion for driving the tip of an entry device as described. The description of the rack and gear structure described and shown herein is not intended to represent the only way that such translation can be accomplished. All conventional techniques within the knowledge of one skilled in the art are considered within the scope of the invention.

FIG. 5 illustrates another feature of the invention. In this embodiment, the rack and gear structure, as well as the trigger of FIGS. 1-4, have been eliminated. These features have been replaced with a power source, such as drive motor 54. The power source may comprise any conventional source suitable for driving the rotation of the hub, such as a source for generating electrical, battery or pneumatic power. A suitable actuator, such as button 55, may be provided to selectively activate, and deactivate, drive motor 54. Upon actuation, the drive motor operates in well known fashion to cause sheath 12 to rotate. Although the translational mechanism and trigger have been removed from the embodiment shown in FIG. 5, this need not be the case. Rather, vessel entry device 10 can be provided with both a manual operation (such as via trigger 36 and translation mechanism 34) and a powered operation (such as via drive motor 54). In this case an operator can selectively utilize either, or both, of these features during a particular vessel entry procedure.

Although FIGS. 1-5 illustrate versions of handles that may comprise a part of the inventive vessel entry device 10, the handles illustrated and described herein are merely examples of the types of handles that may be used. When following the teachings of the present invention, those skilled in the art can readily select other handle designs that will be effective for use in vessel entry. In addition, as stated, the inventive vessel entry device need not necessarily even include a handle, as the sheath member can be manually actuated if desired.

As illustrated in FIGS. 1 and 4-5, a tip 18 is provided at the distal end of sheath 12, and more particularly, at the distal end of inner sheath member 14 when respective inner and outer sheath members are present. Sheath 12 may be constructed in a manner such that distal tip 18 is an integral part of the sheath; however, it is preferred that tip 18 comprises a discrete element joined to the distal end of inner sheath member 14.

For use in a lead removal device, such as the devices disclosed in the incorporated-by-reference application Ser. No. 11/404,666, a sheath will normally have a flexible distal portion. The distal portion comprises the leading end that must be capable of traversing the tortuous pathways of the vessel. Without this flexibility, the device would not generally be able to traverse the pathways to arrive at the target location. However, when it is desired to insert the device through the wall of a body vessel in order to access the interior vessel pathway, the flexibility of the distal end portion of the previous device may render it impossible to pass the device through the wall, and particularly, through scar tissue and/or calcifications that may have built up around the opening and the lead protruding therethrough. In order to position the tip of these flexible devices described in the incorporated-by-reference application over the desired entry point into the vessel, the physician often needs to grasp the device close to the distal tip by hand and direct it to the proper position. However, proper positioning may be problematic; as the physician's view may be blocked by his or her hand at the distal end of the device. The physician then must force the tip through the opening and the scar tissue or calcifications. Manipulation of the device, such as by pushing or turning, may require the physician to also grasp the proximal end of the device. Therefore, two hands are typically required to operate such devices.

The sheath of the inventive vessel entry device need not have the flexibility of the sheaths typically used in lead removal devices. As stated above, in many instances such flexibility would be detrimental, as it would require the user to use two hands to force the tip through the vessel wall. With a less flexible sheath, additional torque may be applied to the sheath such that the distal tip may enter the vessel upon application of less force than is required with the more flexible sheath. In addition, such an operation may typically be carried out by the operator using only a single hand, thus freeing the other hand for related tasks.

FIG. 6 illustrates a side view, partially in section, of one embodiment of an inner sheath member 14. FIG. 6A is an enlarged view of the distal end 62 of inner sheath member 14. In the embodiment shown, sheath member 14 comprises an outer polymeric surface 63 formed of a semi-rigid polymeric material, such as nylon or polyester, that encapsulates an optional reinforcing member, such as a braided wire 64. Generally, it is preferred to use a rigid or semi-rigid polymeric material, otherwise an unreasonably thick wall may be necessary to obtain sufficient stiffness for the sheath to pierce the opening in the vessel wall. Those skilled in the art can readily determine an appropriate sheath material depending on the intended use of the device.

When present, the braid is typically made of stainless steel round wire of about 0.004 inch in diameter. Those skilled in the art will appreciate that other conventional reinforcing materials, such as nitinol, may be substituted, and other cross-sectional geometries may also be used. When present, the braid offers enhanced torsional strength to the sheath, while the polymeric jacket provides bending and compressional stiffness. In the preferred embodiment shown, the braid terminates at least about 0.125 inch from the respective distal ends of the sheath, to prevent projection of the braid wire outside of the polymer. Preferably, inner sheath member 14 is about two to six inches in length, and more preferably, about four inches in length.

Typically, sheath member 14 will have a diameter of about 9 or 11 French, although sheaths of larger or smaller diameter may be used for a particular purpose. With an 11 French diameter sheath, for example, sheath member 14 will preferably be fabricated from nylon. This sheath exhibits a bending stiffness of between about 7 and 9 pound-inch$^2$. In this case, a bending stiffness of above 8 pound-inch$^2$, and preferably about 8.3 pound-inch$^2$ will generally provide best results. Those skilled in the art will appreciate that the stiffness of the sheath will vary depending on factors such as the thickness of the sheath, the presence or absence of a reinforcing member, and the composition of the sheath. In each case, however, the sheath should have a stiffness such that the vessel entry device can be advanced through the vessel opening and scar tissue or calcifications, through manipulation of the proximal end only of the sheath (with or without a handle).

When present, outer sheath member 16 preferably comprises a flexible polymeric material, such as PTFE, having one end beveled and the other end square. In this manner, the physician has the option of using either end as the distal end.

FIG. 7 illustrates one embodiment of a tip 70 that may be joined to the distal end of the sheath of the inventive vessel entry device. FIG. 8 illustrates a longitudinal cross-sectional view of tip 7. Typically, the tip is bonded, adhered, or otherwise affixed to the distal end of a sheath in a secure manner, such that the tip will not disengage under normal conditions encountered during use. In one preferred embodiment, a small diameter proximal end portion 71 of tip 70 may be affixed to the inner surface at the distal end of the sheath, such as inner sheath member 14 in the embodiment of FIGS. 1-5. Those skilled in the art will appreciate that other common means of securely affixing a distal tip to the distal end of a device, such as the sheath described herein, can be substituted.

In the embodiment of FIG. 7, small diameter proximal end portion 71 of tip 70 includes one or more optional rings 72 fitted along the outer surface of proximal end portion 71. When more than one ring is present, rings 72 are preferably aligned in order of increasing width of said ring body in the direction of the distal tip portion. Providing rings having a smaller width in the proximal direction minimizes the stresses in the sheath at the area of joinder of the sheath and the tip, where stresses resulting from tension, torsion, and bending tend to be the highest. If desired, rings 72 may be provided with one or more cut-outs 73 along the circumference of rings 72. Cut-outs 73 serve to hinder rotation of the tip when the proximal tip portion is positioned inside the distal portion of the sheath, such as inner sheath member 14.

Although the preferred embodiment illustrated above comprises rings 72 for engagement with the inner surface of the sheath, those skilled in the art will appreciate that other conventional attachment and/or securement mechanisms may be substituted in a particular case. For example, rather than rings, the proximal end of tip 70 can be provided with one or more barbs along the proximal length of the tip, which barbs are configured to attach to the inner surface of the sheath. As another alternative, the proximal end of tip 70 can be provided with a roughened outer surface for facilitating attachment with the inner surface of the sheath by well-known means, such as adhesion. In this case, the outer surface of the cutting tip may be roughened by any conventional process, such as bead blasting and etching. As is well known, the use of a roughened outer surface enables an improved connection to be formed between the cutting tip and the sheath.

The embodiment of FIG. 7 also illustrates a series of radially outwardly directed projections, such as helices 75, on the outer surface of tip 70. Preferably, tip 70 includes four helices 75 spaced about 90 degrees apart along the outer surface of distal end portion 61 of the tip. The radially outer projections, such as helices 75, primarily disrupt (alter or move aside) the body tissue encountered during insertion and rotation of the vessel entry device. Preferably, the leading (distal) end of the tip is structured such that the tip primarily, if not completely, disrupts, rather than cores or cuts, enough of the obstruction in the vicinity of the lead to allow the sheath to pass through the obstruction. By gently disrupting the obstruction, rather than cutting or coring it, the tips have a reduced propensity to cut a lead or breach a vessel wall. Disrupting-type tips are generally preferred for use with rotary action devices. In this case, the device disrupts in a forward direction along the path of the structure, such as a pacing lead, targeted for removal, while at least substantially avoiding cutting in an outward or inward direction. Since entry is gained into the blood vessel along perforations defined by the pacing lead, no new holes are being punched into the vessel.

While disruption of soft tissue by the tip configured as described herein may often be adequate for loosening the tissue enveloping the lead, there are occasions when a considerable amount of tough and calcified tissue may be present at the entrance of the lead to the blood vessel. To loosen this tenacious tissue, some cutting or coring of the tissue may be necessary. In the inventive device, the combination of a specially configured tip, and a sheath capable of delivering high torque while allowing the physician to control the direction of push using one hand, enables the physician to penetrate the tip into this tissue in a controlled manner.

Although the disruptors are shown in the figure as helices, this is only one example of a type of disrupter element that may be present on the tip portion. As alternatives, the disrupter may comprise linear, or non-linear, segments of other configurations, which segments may or may not be continuous, and may have any cross-sectional dimension. Similarly, the disruptor elements may point in any direction, or in no direction, in which case the disrupter element can have a configuration such as a dot or a circle.

Preferably the disruptors, such as helices 75, originate at or near the distal edge 76 of tip 70, and extend proximally therefrom. Although continuous helices may be provided, the embodiment illustrated in FIG. 7 includes helices 75 that are discontinuous. By "discontinuous" is meant that an individual helix has one or more spaces, or voids, 78 along the length of the particular helix. The discontinuous helices provide the device with a heightened ability to engage surrounding scar tissue or calcifications. The structure helps the device draw itself forward and through subcutaneous tissue prior to the vessel, and then through difficult adhesions in the area where venous entry occurs. Preferably, helices 75 extend in the proximal direction to a junction 77 of the larger diameter distal end portion 79 and the smaller diameter proximal end portion 71.

The tip portion of the inventive device may be fabricated from a material having sufficient strength and rigidity to cut through or otherwise disrupt obstructions encountered during a lead removal. Metals and metal alloys, such as stainless steel, nitinol and titanium, are particularly preferred tip materials. Such tips may be formed from known techniques, such as machining and metal injection molding. Those skilled in the art will appreciate that other compatible materials may be used in place of metal or metal alloys. For example, a fiber-reinforced polymer, such as fiber-reinforced polypropylene, may be used. Non-limiting examples of suitable fiber reinforcements include glass and carbon fibers. In an embodiment wherein the tip is formed as an integral portion of the sheath, the tip may conveniently be formed of a polymer, such as polypropylene, and may be molded onto the end of a sheath formed from a polymer that is compatible to the polymer of the tip material.

One example illustrating the use of the inventive vessel entry device 10 is shown in FIG. 9. FIG. 9 illustrates a body vessel 100 with a cardiac lead 102 protruding from an opening 101 in the vessel. Typically, the lead is severed from the pacemaker or other device external of the vessel to form a free end 103. If desired, a locking stylet (not shown) may be inserted into the lead at the free end. The lead (and locking stylet when present) can then be inserted through and beyond the proximal end of sheath member 14 of the vessel entry device 10.

Typically, the vessel opening through which the cardiac lead 102 passes has closed around the lead with the passage of time, and scar tissue and/or calcifications may have formed at that point. As a result, a flexible lead extraction device cannot generally be pushed through the opening and scar tissue or calcifications, at least not without the necessity for the physician to use two hands and a considerable amount of pushing force. With the known device, one of the physician's hands must be at the distal end grasping the device and controlling its direction of push and forcing it through the scar tissue, and the other hand is grasping the proximal end. At this point, the sheath is outside the blood vessel and is therefore unguided. With the inventive vessel entry device, the more rigid device is forced against the scar tissue or calcification at the opening. Due to the rigidity of the sheath member 14, as well as the configuration of the tip 18, the sheath is able to exert sufficient torque such that the sheath penetrates the opening and/or the scar tissue or calcifications without the necessity of the physician using two hands. The physician can control the direction of push from the handle 20, while actuating the rotation of the sheath necessary to effect penetration of the scar tissue, using just one hand. Use of a single hand improves the physician's line of visibility to the opening, and additionally, frees the physician's other hand for other purposes.

In some cases, once freed from the opening and/or scar tissue, the lead can then simply be pulled out of the vessel. If, however, the lead is further encapsulated by obstructions within the vessel, the vessel entry device can be removed. Another device, such as the lead extraction device described in the incorporated-by-reference application Ser. No. 11/404, 666, can then be inserted over the lead through the entry hole formed in the vessel to disrupt, or cut, the lead from the obstructions.

If desired, selected portions of the vessel entry devices described herein, such as the tip portion, can be provided with means for x-ray or fluoroscopic vision. Such means are well known in the art, and may include, for example, the incorporation of a radiopaque band, or the inclusion of radiopaque particles in the selected portion. As still another alternative, the tip can be formed (in whole or in part) of a metal or metallic alloy to provide such visibility. In general, increased visibility of the tip is beneficial because it allows the operator to determine the location of the tip at a particular point in time, and also provides the operator with the ability to track the position and orientation of the tip with reference to the lead body.

Those skilled in that art will appreciate that the foregoing detailed description should be regarded as illustrative rather than limiting, and that it should be understood that it is the following claims, including all equivalents, that are intended to define the spirit and scope of this invention.

The invention claimed is:

1. An entry device for providing access to an interior of a body vessel through an opening in a wall of the vessel for removing an elongated indwelling structure therefrom, said elongated structure extending through the opening such that a distal end of said elongated structure is disposed along the body vessel interior and a proximal end of said elongated structure extends exteriorly to the body vessel, wherein at least a portion of the body vessel wall opening is enclosed around said elongated structure in a manner to impede a removal of said elongated structure from the vessel, the device comprising:

an elongated sheath and a tip positioned at a distal end of said sheath, said elongated sheath and tip having respective passageways extending therethrough, said passageways sized and aligned such that said elongated structure is receivable therein, said elongated sheath having a rigidity sufficient to permit initial entry of said tip through the enclosed portion of the vessel wall opening by at least one of rotational and axial movement of a proximal end of said sheath, said tip having a radially-outwardly directed disruptor disposed along an outer surface thereof, said disruptor configured for achieving said initial entry through said enclosed portion of the vessel wall, said disruptor comprising a plurality of helices extending along the outer surface of said tip and projecting in a generally radially outward direction from said surface, said helices originating at a distal edge of said tip and extending proximally therefrom, wherein said helices each comprise a uniform cross-section along a length thereof, and wherein said helices each comprise a distal end that terminates adjacent to a distal-most edge of the tip and projects radially-outwardly from the outer surface of said tip, the distal ends of said helices each comprising a planar distal face that is disposed within a transverse plane defined by the distal edge of the tip and oriented perpendicularly to a longitudinal axis of the tip.

2. The entry device of claim 1, wherein said sheath comprises respective coaxial inner and outer sheath members.

3. The entry device of claim 2, wherein said inner sheath member includes a reinforcing member disposed along a length thereof; and said outer sheath member comprises PTFE.

4. The entry device of claim 1, further comprising a handle configured for engagement with a proximal end of said sheath.

5. The entry device of claim 4, wherein said handle includes an actuator and a drive mechanism responsive to said actuator, said drive mechanism operable for selectively translating input of said actuator into said at least one of rotation and axial movement of said sheath.

6. The entry device of claim 1, wherein said elongated sheath is formed of nylon or polyester, and has a bending stiffness of at least about eight pound-inch2.

7. The entry device of claim 1, wherein at least some of said helices are discontinuous along said surface.

8. The entry device of claim 1, wherein said tip has a proximal end, said proximal end being securely affixed to said sheath distal end.

9. The entry device of claim 8, wherein said tip proximal end is sized such that said tip proximal end is receivable in said sheath distal end for affixation.

10. The entry device of claim 1, wherein at least some of said helices include one or more void spaces along an axial length thereof.

11. The entry device of claim 10, wherein said tip has a smaller diameter proximal end and a larger diameter distal end, said smaller diameter proximal end sized and configured for engagement with an inner surface of said sheath distal end, said larger diameter distal end having said disruptor disposed therealong, said helices extending from said tip distal end to a junction of said smaller diameter tip proximal end and said larger diameter tip distal end.

12. The entry device of claim 11, wherein said tip small diameter proximal end comprises a plurality of rings spaced along said tip outer surface.

13. The entry device of claim 1, wherein said plurality of helices comprises four helices spaced about 90 degrees apart along said tip outer surface.

14. The entry device of claim 1, wherein said elongated sheath has a length and rigidity sufficient to permit said initial entry of said tip through the enclosed portion of the vessel wall opening by rotational movement of said sheath, said sheath length being from about two to six inches, and said sheath rigidity being from about 7 to 9 pounds per square inch.

15. The entry device of claim 14, wherein said sheath is formed of nylon, said sheath having a diameter of about 11 french and a bending stiffness of about 8.3 pound-inch$^2$.

16. The entry device of claim 1, wherein said tip includes an inner surface defining said tip passageway, said tip further comprising a smooth transition from said distal edge to said tip passageway.

17. The entry device of claim 16, wherein said transition includes an inside radius from said edge to said inner passageway.

18. The entry device of claim 1, wherein the tip comprises a sharpened distal edge defined by a chamfered surface disposed along one of the outer surface or inner surface of said tip.

19. A method of achieving initial entry to a body vessel for removing an elongated indwelling structure therefrom, the elongated indwelling structure having a distal end disposed within the body vessel and a free proximal end extending through an opening in the vessel, and wherein a vessel wall portion defining the opening is enclosed around the elongated structure in a manner to inhibit removal of the elongated structure from the vessel, the method comprising:

positioning a vessel entry device over the elongated structure free proximal end for initial entry into said vessel at said enclosed vessel wall portion, said device comprising an elongated sheath and a tip positioned at a distal end of the sheath, the elongated sheath and tip having respective passageways extending therethrough, the passageways sized and aligned such that the proximal end of the elongated structure is receivable therein, the elongated sheath having a rigidity sufficient to permit said initial entry of said tip through said vessel wall portion by at least one of rotational and axial movement of a proximal end of said sheath, said tip configured for initial entry through said vessel wall portion and having a radially-outwardly directed disruptor disposed along an outer surface thereof, said disruptor configured for achieving said initial entry through said vessel wall, said disruptor comprising a plurality of helices extending along the outer surface of said tip and projecting in a generally radially outward direction from said surface, said helices originating at a distal edge of said tip and extending proximally therefrom, wherein said helices each comprise a uniform cross-section along a length thereof, and wherein said helices each comprise a distal end that terminates adjacent to a distal-most edge of the tip and projects radially-outwardly from the outer surface of said tip, the distal ends of said helices each comprising a planar distal face that is disposed within a transverse plane defined by the distal edge of the tip and oriented perpendicularly to a longitudinal axis of the tip; and advancing the tip of the vessel entry device through said vessel wall portion enclosed around the elongated structure to free the elongated structure from the vessel wall portion.

20. The method of claim 19, wherein said vessel entry device further comprises a drive mechanism, the method further including the step of actuating the drive mechanism to provide at least one of rotational and axial movement to said sheath.

21. The method of claim 19, further including the steps of advancing the sheath over the elongated structure and through the opening; and removing the elongated structure from the body vessel through the tip and sheath.

22. The method of claim 19, wherein said plurality of helices along said outer surface comprises four helices.

23. The method of claim 22, wherein at least some of said helices are discontinuous along said surface.

24. The method of claim 19, further including the steps of: removing the vessel entry device from the vessel wall portion; and inserting a lead extraction device into the vessel over the proximal end of the freed elongated structure for disrupting the elongated structure from obstructions encountered within an interior pathway of the vessel.

* * * * *